United States Patent [19]

Oshima et al.

[11] 4,343,955

[45] Aug. 10, 1982

[54] METHOD FOR THE PREPARATION OF CIS-ALKYLCYCLOHEXANOLS

[75] Inventors: Mituyoshi Oshima, Joetsu; Jun Yoshimoto, Odawara, both of Japan

[73] Assignees: Shin-Etsu Chemical Co., Ltd.; Sankio Chemical Co., Ltd., both of Tokyo, Japan

[21] Appl. No.: 17,892

[22] Filed: Mar. 6, 1979

[30] Foreign Application Priority Data

Mar. 13, 1978 [JP] Japan .................................. 53-28524

[51] Int. Cl.³ ............................................. C07C 35/08
[52] U.S. Cl. ........................................ 568/834; 568/835
[58] Field of Search ................................ 568/834, 835

[56] References Cited

U.S. PATENT DOCUMENTS 3,055,840  9/1962  Koeh ..................................... 568/835
4,067,915  1/1978  Yasuhama et al. ................... 568/835

FOREIGN PATENT DOCUMENTS 48-4449  1/1973  Japan ..................................... 568/834

*Primary Examiner*—Paul J. Killos
*Attorney, Agent, or Firm*—Hopgood, Calimafde, Kalii, Blaustein & Judlowe

[57] ABSTRACT

An improved method for selectively hydrogenating an alkylphenol to produce the corresponding cis-alkylcyclohexanol by employing a solid catalyst is disclosed. The catalyst useful in this method is a ruthenium catalyst supported on an alumina carrier. This catalyst exhibits excellent reactivity, selectivity and durability in the catalytic hydrogenation compared to conventional rhodium or ruthenium catalysts, such as ruthenium oxide and ruthenium catalysts supported on carbon. The alkylcyclohexanol product contains so much cis-isomer that it is suitable as such for use as an intermediate for the synthesis of varous chemicals, such as perfumes.

7 Claims, No Drawings

METHOD FOR THE PREPARATION OF CIS-ALKYLCYCLOHEXANOLS

BACKGROUND OF THE INVENTION

The present invention relates to a method for the preparation of a cis-alkylcyclohexanol or, more particularly, to a method for the preparation of an alkylcyclohexanol by the catalytic hydrogenation of the corresponding alkylphenol with hydrogen in which the yield of the cis-isomer relative to the trans-isomer is markedly increased.

Alkylcyclohexanols are useful compounds as an intermediate for the synthesis of various kinds of perfumes, medicines and other organic chemicals. Of the two stereoisomers of the alkylcyclohexanols, viz. the cis- and trans-isomers, the cis-isomers are particularly useful as a perfume as such or as the intermediate compound for the synthesis of perfumes. Therefore, one of the more important problems in the technology of organic synthesis is to obtain an aklylcyclohexanol product rich in the cis-isomer.

Alkylcyclohexanols are prepared most conveniently by the catalytic hydrogenation of the corresponding alkylphenols with hydrogen. Several methods have been proposed as directed to the enhancement of the cis/trans selectivity, among which is known a method utilizing a rhodium catalyst, e.g. metallic rhodium, rhodium-platinum and rhodium-ruthenium, supported on certain catalyst carriers such as carbon and the like (see, for example, Japanese Patent Publication No. 42-13938 and U.S. Pat. No. 2,927,127). This method of rhodium-catalyzed hydrogenation is disadvantageous, not only because of the expense of using rhodium, but also because the poor selectivity with respect to the cis-isomers. The selectivity problem is particularly troublesome when the hydrogenation reaction is undertaken at an elevated temperature in order to increase the reaction velocity. Furthermore, when the catalyst is to be used repeatedly in numbers of runs, it has been found that the catalyst is not sufficiently durable.

In addition, the reaction products obtained by the rhodium-catalyzed hydrogenation of alkylphenols contain large amounts of alkylbenzenes as the decomposition products of the hydrogenation reaction as well as considerable amounts of unidentified impurities with consequent low yields of the desired alkylcyclohexanols based on the starting alkylphenols. There is also difficulty in subsequent purification, especially, when the alkylcyclohexanols are intended to be used in perfumery so that the rhodium-catalyzed hydrogenation is somewhat questionable industrially.

Another approach for improving the cis/trans ratio of the alkylcyclohexanols is the use of ruthenium catalyst as disclosed in Maruzen Sekiyu Giho (Technical Bulletin of Maruzen Petroleum Co.), No. 16, pp. 77–87 (1971), according to which the ruthenium catalyst is used in a form of ruthenium oxide or a ruthenium catalyst supported on a carbon carrier. This method of ruthenium-catalyzed hydrogenation gives an improved cis/trans ratio in comparison with the rhodium-catalyzed hydrogenation reaction but the durability of the catalyst activity is still unsatisfactory necessitating frequent use of fresh catalysts. It is also desirable to decrease the amount of alkylbenzenes as a by-product contained in the hydrogenation products obtained with the above mentioned ruthenium oxide or ruthenium/-carbon catalyst for the method to be of practical value in the technology of perfumery.

SUMMARY OF THE INVENTION

It is therefore an object of the present invention to provide a novel and improved method for the preparation of an alkylcyclohexanol by the catalytic hydrogenation of the corresponding alkylphenol, in which the selectivity for the cis-isomer is markedly enhanced relative to the trans-isomer. More particularly, the inventive method proposes a ruthenium-catalyzed hydrogenation of an alkylphenol according to which the above described problems in the prior art methods with respect to the selectivity of the catalysts as well as the durability of the catalyst are satisfactorily eliminated.

Thus, the method of the present invention comprises hydrogenating an alkylphenol represented by the general formula

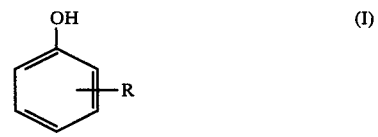
(I)

where R is an alkyl group having from 1 to 4 carbon atoms, in the presence of a ruthenium catalyst supported on an alumina carrier to give a cis-alkylcyclohexanol represented by the general formula

(II)

where R has the same meaning as defined above, with high selectivity and high yield, in which remarkably extended catalyst life is obtained.

DETAILED DESCRIPTION OF THE PREFERRED EMBODIMENTS

The starting material used in the inventive method is an alkylphenol represented by the above given general formula (I), in which the symbol R stands for an alkyl group having from 1 to 4 carbon atoms such as methyl, ethyl, propyl and butyl groups including the isomeric groups of propyl and butyl, i.e. n-propyl, iso-propyl, n-butyl, sec-butyl, tert-butyl and iso-butyl groups. The position of nuclear substitution of the alkyl group relative to the phenolic hydroxy group is not limitative including ortho-, meta and para-positions. The examples of the alkylphenols suitable for the inventive method are: 3-methylphenol, 4-methylphenol, 2-tert-butylphenol, 4-tert-butylphenol, 2-ethylphenol and the like.

The ruthenium catalyst supported on an alumina carrier is prepared by conventional dry or wet processes known in the art. Namely, the alumina carrier is dipped in an aqueous solution of ruthenium chloride ($RuCl_3$), dried and subjected to reduction in a stream of hydrogen or in formalin whereby the ruthenium salt is reduced to the metallic state. The alumina carrier may have a sufficiently large specific surface area ranging, for example, from 100 to 300 $m^2/g$ and a fine particle size distribution to pass a screen of, for example, 100 mesh or finer.

The amount of ruthenium supported on the alumina carrier is usually within the range from 0.1 to 20% by weight or, preferably from 0.5 to 10% by weight based on the total amount of the catalyst. The use of less than 0.1% ruthenium would lead to unsatisfactory catalytic activity whereas the use of amounts exceeding 20% by weight would also be undesirable due to the lower activity despite the increased cost of the catalyst.

The amount of the catalyst to be used depends on the ruthenium content of the catalyst and the desired reaction velocity in relation to the kind of the starting alkylphenol but it is usually in the range of from 0.01 to 1.0% by weight of ruthenium based on the amount of the alkylphenol.

The hydrogenation reaction according to the present invention is carried out in a closed vessel, i.e. autoclave, into which the alkylphenol as the starting material is introduced together with the catalyst and, after the air inside the vessel has been purged with a suitable inert gas, hydrogen is compressed into the vessel to a desired pressure and the reaction mixture is heated to a predetermined reaction temperature. As the temperature is increased with stirring of the reaction mixture, the hydrogenation reaction begins and predetermined pressure is maintained by periodically supplying hydrogen to compensate for the hydrogen absorption.

The reaction temperature is in the range from 40° C. to 200° C. or, preferably, from 60° C. to 180° C. Temperatures higher than 200° C. are undesirable due to the decreased cis/trans selectivity even though the reaction velocity is increased. The pressure of hydrogen is desirably as high as possible in order to ensure high reaction velocity. The pressure is preferably in excess of 5 kg/cm$^2$G or, more preferably, 10 kg/cm$^2$G. The time required for completion of the reaction depends on the reaction temperature, hydrogen pressure, activity of the catalyst, the kind of the alkylphenol and other factors but the reaction may be terminated when no further absorption of hydrogen takes place. A reaction time less than 4 hours is usually sufficient for completion of the reaction.

It is optional or sometimes advantageous to have the alkylphenol diluted with a suitable solvent inert to hydrogenation such as aliphatic alcohols and hydrocarbons. A mixed solvent of an alcohol and water is recommendable for obtaining higher reaction velocity.

After completion of the reaction and cooling down of the vessel to room temperature, the reaction mixture is taken out of the vessel and the catalyst is separated from the liquid components by filtration or centrifugal separation. The thus recovered catalyst can be used repeatedly as such without particular re-activation in the subsequent runs in which the selectivity for the cis-isomer is maintained at as high as 75% or more even after 30 cycles of the repeated hydrogenation runs.

The liquid reaction mixture separated from the catalyst is rich in the cis-isomer of the alkylcyclohexanol so that the resultant reaction mixture may be used as the intermediate of the final desired compound without further purification. For example, 4-tert-butylcyclohexanol obtained by the inventive method contains 75% or more of the cis-isomer and can be reacted with acetic anhydride or glacial acetic acid to give 4-tert-butylcyclohexyl acetate having excellent orris-like fragrance useful as a perfume.

The following examples and comparative examples will demonstrate the advantages of the inventive method over the prior art method but do not limit the scope of the invention.

EXAMPLE 1

Into a stainless steel autoclave of 200 ml capacity equipped with an electromagnetic strirrer were introduced 45 g of 4-tert-butylphenol, 36 ml of ethyl alcohol, 9 ml of water and 0.45 g of a ruthenium catalyst supported on an alumina carrier, of which the ruthenium content was 5% by weight, and, after the air inside the autoclave had been purged with nitrogen, the temperature was increased up to 100° C. with pressurization with hydrogen to a pressure of 40 kg/cm$^2$G where the temperature and the pressure was maintained with periodic supply of additional volumes of hydrogen under agitation and with the velocity of the stirrer at 1000 r.p.m. for about 4 hours.

After the end of the above reaction time, when no further absorption of hydrogen was taking place, the reaction mixture was cooled and taken out of the autoclave to give about 46 g of the reaction product by the removal of the catalyst by filtration and the solvents by evaporation. The thus obtained reaction product was analyzed by gas chromatography. The yield of the cis- and trans-4-tert-butylcyclohexanols was 74.8 and 24.9% by weight, respectively, with only about 0.3% by weight of tert-butylbenzene as a by-product.

The above obtained 4-tert-butylcyclohexanol was subjected to reaction with acetic anhydride to give 4-tert-butylcyclohexyl acetate which had a very pleasant orris-like fragrance suitable for use as a perfume of high quality.

EXAMPLE 2

Into the same autoclave as used in Example 1 were introduced 45 g of an alkylphenol as indicated in Table 1 below, 45 ml of n-hexane and 2.25 g of a ruthenium catalyst supported on an alumina carrier, of which the ruthenium content was 10% by weight, and the hydrogenation reaction was undertaken similarly to Example 1 with the reaction temperature at 120° C. and the hydrogen pressure of 60 kg/cm$^2$G for 3 hours. The results of the gas chromatographic analysis undertaken for the reaction products were as set out in Table 1.

TABLE 1

| | Reaction Product, % by weight | | |
|---|---|---|---|
| Alkylphenol | cis-Alkyl-cyclohexanol | trans-Alkyl-cyclohexanol | Alkyl-benzene |
| 3-Methylphenol | 71.3 | 28.6 | 0.1 |
| 4-Methylphenol | 67.2 | 31.8 | 1.0 |
| 2-Ethylphenol | 74.2 | 25.0 | 0.8 |
| 2-tert-Butylphenol | 92.5 | 7.2 | 0.3 |

EXAMPLE 3

Into a stainless steel autoclave of 200 liter capacity were introduced 45 kg of 4-tert-butylphenol and 0.45 kg of a ruthenium catalyst supported on an alumina carrier, of which the ruthenium content was 10% by weight, and the hydrogenation reaction was carried out at 105° C. for 4 hours maintaining the hydrogen pressure of 80 kg/cm$^2$G. After completion of the reaction, the reaction mixture was taken out of the autoclave and the catalyst was separated by hot filtration to give 46.0 kg of the reaction product. The gas chromatographic analysis of the reaction product indicated that the yield of cis-4-tert-butylcyclohexanol, trans-4-tert-butylcyclohexanol and tert-butylbenzene was 74.1, 25.7 and 0.2% by weight, respectively.

The above obtained 4-tert-butylcyclohexanol was reacted with acetic anhydride to give 4-tert-butylcyclohexyl acetate having excellent orris-like fragrance suitable for use as a high-quality synthetic perfume.

The ruthenium catalyst separated from the reaction mixture in the above Example was used as such in a second run of the hydrogenation reaction with the same experimental procedure as in the first run to give almost identical results with respect to the reactivity and selectivity. Similarly, the recovered catalyst was used repeatedly in more than 30 runs of the same hydrogenation reaction showing no marked decrease in the catalytic activity and the cis/trans selectivity.

COMPARATIVE EXAMPLE 1

The same experimental procedure as in Example 1 was repeated except that 2.25 g of a 5% ruthenium catalyst supported on a carbon carrier was used instead of 0.45 g of the ruthenium/alumina catalyst to give 44.8 g of the reaction product. The gas chromatographic analysis of the reaction product indicated that the yield of cis- and trans-4-tert-butylcyclohexanols and tert-butylbenzene was 44.2, 53.9 and 1.9% by weight, respectively.

This reaction product was reacted with acetic anhydride to produce 4-tert-butylcyclohexyl acetate but the thus prepared acetate had a fragrance with a strong cedar-like woody note not suitable as a perfume.

COMPARATIVE EXAMPLE 2

The same experimental procedure as in Example 1 was repeated except that the ruthenium catalyst was replaced with 0.45 g of a rhodium catalyst supported on carbon, of which the rhodium content was 5% by weight, and that the reaction temperature was 50° C. instead of 100° C. The gas chromatographic analysis of the resultant reaction product indicated that the yield of cis- and trans-4-tert-butylcyclohexanols and tert-butylbenzene was 58.7, 40.8 and 0.5% by weight, respectively.

The catalyst separated from the reaction mixture was used in the subsequent runs as recovered to show that the catalytic activity of the catalyst rapidly decreased to an impractically low level after five hydrogenation runs.

COMPARATIVE EXAMPLE 3

The same experimental procedure as in Example 1 was repeated except that 0.45 g of a rhodium catalyst supported on an alumina carrier (of which the rhodium content was 5% by weight), instead of the ruthenium catalyst was used. Also, the reaction temperature was 80° C. instead of 100° C. The gas chromatographic analysis of the reaction product indicated that the yields of cis- and trans-4-tert-butylcyclohexanols and tert-butylbenzene was 56.4, 42.1 and 1.5% by weight, respectively. The second run of the same hydrogenation reaction using the rhodium catalyst as recovered in the above first run resulted in markedly decreased catalyst activity and cis/trans selectivity.

What is claimed is:

1. A method for preparing cis-4-tert-butylcyclohexanol which comprises hydrogenating 4-tert-butylphenol with hydrogen in the presence of a catalyst containing ruthenium supported on an alumina carrier under a superatmospheric pressure of hydrogen and at an elevated temperature.

2. The method of claim 1 wherein the catalyst contains from 0.1 to 20% by weight of ruthenium.

3. The method of claim 1 wherein the elevated temperature is in the range from 40° C. to 200° C.

4. The method of claim 1 or claim 2 wherein the superatmospheric pressure is at least 5 kg/cm$^2$G.

5. The method as claimed in claim 1 wherein the alkylphenol is diluted with a solvent.

6. The method of claim 1 wherein the amount of the catalyst is in the range from 0.01% to 1.0% by weight as ruthenium based on the amount of the alkylphenol.

7. The method of claim 1 wherein the alumina carrier has a specific surface area in the range from 100 m$^2$/g to 300 m$^2$/g and a particle size distribution to pass a screen of 100 mesh opening.

* * * * *